(12) United States Patent
Cerati et al.

(10) Patent No.: US 7,176,696 B2
(45) Date of Patent: Feb. 13, 2007

(54) METHOD OF DETECTING AND ELIMINATING FOREIGN BODIES IN A FLOW OF TOBACCO

(75) Inventors: Luca Cerati, Bologna (IT); Fiorenzo Draghetti, Medicina (IT)

(73) Assignee: G.D S.p.A., Bologna (IT)

( * ) Notice: Subject to any disclaimer, the term of this patent is extended or adjusted under 35 U.S.C. 154(b) by 0 days.

(21) Appl. No.: 10/347,618

(22) Filed: Jan. 22, 2003

(65) Prior Publication Data

US 2003/0137312 A1 Jul. 24, 2003

(30) Foreign Application Priority Data

Jan. 21, 2002 (IT) ...................... BO2002A000038

(51) Int. Cl.
  *G01R 27/04* (2006.01)
  *G01R 27/34* (2006.01)
(52) U.S. Cl. ...................... 324/633; 324/634; 324/640; 324/643
(58) Field of Classification Search ................ 324/634, 324/640, 643, 633
  See application file for complete search history.

(56) References Cited

U.S. PATENT DOCUMENTS

| | | | |
|---|---|---|---|
| 4,707,652 A | 11/1987 | Lowitz | ........................ 324/631 |
| 4,942,363 A * | 7/1990 | Lowitz | ........................ 324/631 |
| 5,476,108 A | 12/1995 | Dominguez et al. | ........ 131/108 |
| 5,623,952 A * | 4/1997 | Hausler | ........................ 131/281 |
| 5,736,864 A * | 4/1998 | Moller | ........................ 324/633 |
| 5,977,780 A | 11/1999 | Herrmann | .................... 324/640 |
| 6,037,591 A * | 3/2000 | Neri et al. | ................ 250/341.1 |
| 6,163,158 A | 12/2000 | Moeller et al. | ............. 324/633 |
| 6,452,404 B2 * | 9/2002 | Moeller et al. | ............. 324/633 |

FOREIGN PATENT DOCUMENTS

| | | |
|---|---|---|
| DE | 19705260 | 8/1997 |
| DE | 10037180 | 1/2002 |
| EP | 0902277 | 3/1999 |
| IT | 1286764 | 7/1998 |

\* cited by examiner

*Primary Examiner*—Anjan Deb
*Assistant Examiner*—John Teresinski
(74) *Attorney, Agent, or Firm*—Harbin King & Klima

(57) ABSTRACT

In a method of detecting and eliminating foreign bodies in tobacco, a flow of tobacco advances first through a preparation zone where it is gathered into a continuous ribbon of tobacco filler, then through a forming station at which the filler is used to fashion a continuous cigarette rod, and finally through a cutter device that divides the rod into cigarette sticks; the advancing flow is directed at a given point through a detection device and exposed to electromagnetic radiation of microwave frequency emitted and received in such a way as to generate output signals reflecting any variations in moisture content along the flow of tobacco, caused by the inclusion of foreign bodies and associated with given portions of the flow each coinciding with a singly identifiable cigarette stick.

20 Claims, 2 Drawing Sheets

METHOD OF DETECTING AND ELIMINATING FOREIGN BODIES IN A FLOW OF TOBACCO

BACKGROUND OF THE INVENTION

The present invention relates to a method for the detection and elimination of foreign bodies in a flow of tobacco.

In particular, the present invention relates to a method of detecting and eliminating foreign bodies such as might be contained within a flow of filler material used conventionally in the manufacture of tobacco products.

The invention finds application, advantageously, in the art field concerned with the detection of non-metallic foreign matter that may be present either in a ribbon of loose tobacco filler or in a continuous cigarette rod.

Foreign bodies present within a flow of shredded tobacco filler, destined for use in the manufacture of tobacco products, can be harmful to the smoker in that when burned they may give off toxic or at all events disagreeable substances. It is therefore particularly important that tobacco products should not contain these foreign bodies.

Foreign matter of a ferrous nature is removed normally from a mass of shredded tobacco by causing a flow of the tobacco, however ordered, to advance along a path passing close to a magnet.

Other foreign matter including metallic materials can be detected utilizing infrared rays or other types of electromagnetic radiation, directed in such a manner that the radiated energy is impeded, diverted or reflected by the metallic foreign body.

Satisfactory results have also been achieved in the detection of non-metallic foreign bodies using beta or gamma rays, albeit with the drawback that these are generated by a radioactive and therefore potentially hazardous source.

As an alternative to these types of radiation, the prior art also embraces the use of devices as disclosed in Italian patent n° 1 286 764, designed to emit electromagnetic radiation in the infrared range and equipped with special filters, which are able to generate different beams of electromagnetic radiation with wavelengths selected according to the particular type of foreign body being detected (wood, plastic, glass, etc.).

The method in question has been found unreliable however, inasmuch as these types of electromagnetic radiation appear to be influenced by the physical properties of the tobacco, for example the length and color of the fibers.

The object of the present invention is to provide a method of detection and rejection unaffected by the aforementioned drawbacks.

SUMMARY OF THE INVENTION

The stated object is realized, according to the invention, in a method of detecting and eliminating foreign bodies in a flow of tobacco, comprising the steps of advancing the flow along a predetermined path in a predetermined direction, passing from a feed station to a preparation zone in which the selfsame flow is gathered into a continuous ribbon of tobacco filler, thence through a forming station at which the tobacco filler is incorporated into at least one continuous cigarette rod, and through a cutter device by which the continuous cigarette rod is divided into cigarette sticks.

The method disclosed includes the further steps of exposing the flow of tobacco to electromagnetic radiation of selected frequency, and sensing an output signal indicative of variations in moisture content along the flow of tobacco, occasioned by the presence of foreign bodies within the selfsame flow.

BRIEF DESCRIPTION OF THE DRAWINGS

The invention will now be described in detail, by way of example, with the aid of the accompanying drawings, in which.

DESCRIPTION OF THE PREFERRED EMBODIMENTS

Figure 1:
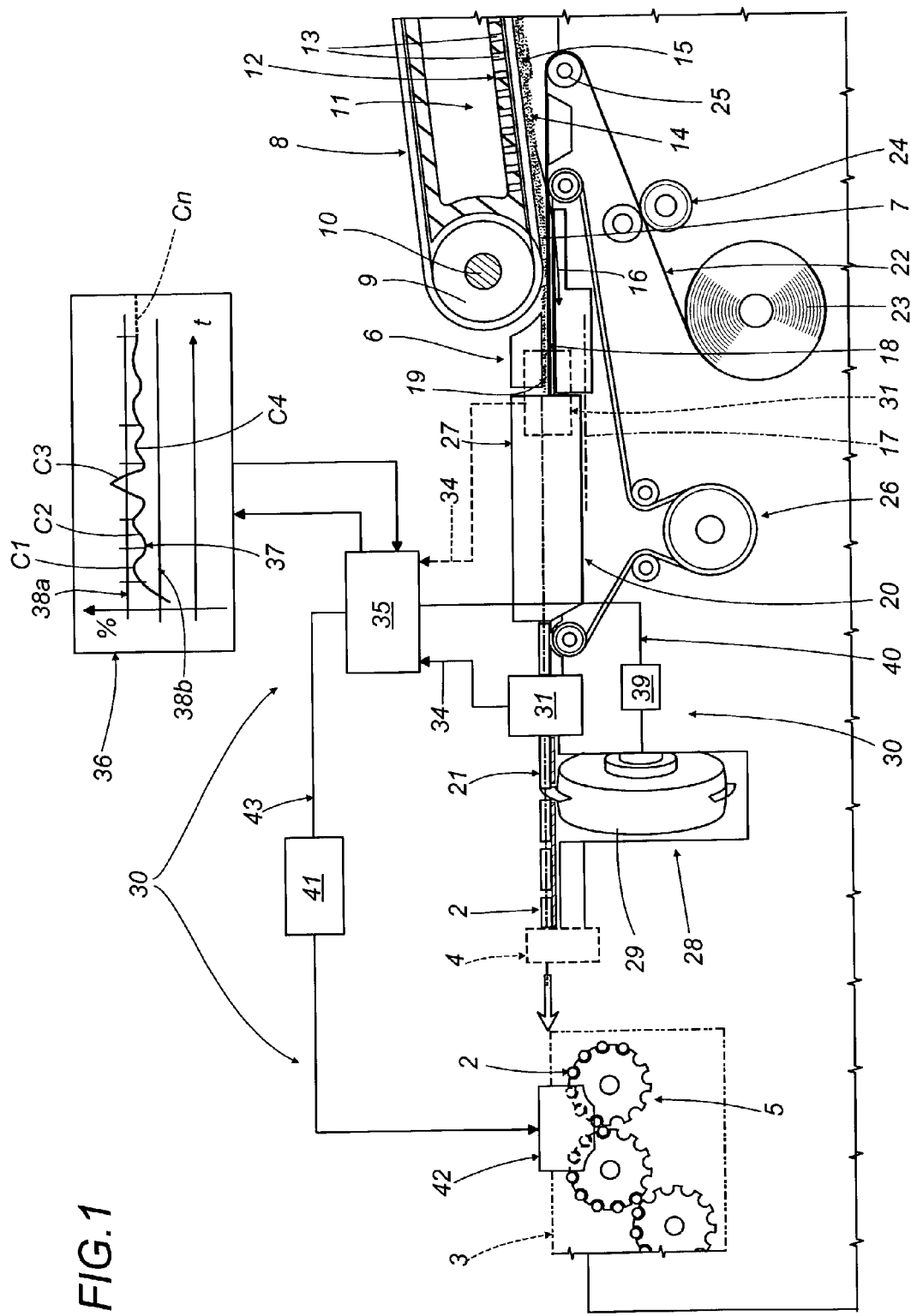
FIG. 1 illustrates a machine equipped with a device able to implement the method according to the present invention, viewed schematically in a side elevation and partly as a block diagram.

Referring to FIG. 1 of the drawings, 1 denotes a portion, in its entirety, of a cigarette maker, and more exactly a machine for fashioning cigarette sticks 2, comprising two twin lines extending one alongside the other (one only of which is shown in FIG. 1) and designed conventionally to operate in parallel.

3 denotes a portion of a filter tip attachment linked to the cigarette maker by way of a device 4 of which the function is to direct the cigarette sticks 2 onto a first roller 5 of the filter tip attachment 3.

The machine 1 is equipped with a feed station 6 through which a continuous flow 7 of tobacco is directed by means of an aspirating conveyor belt 8 looped around pulleys 9 positioned one at either end (one only of which is shown in FIG. 1) and rotatable clockwise, as viewed in FIG. 1, about respective axes 10 extending transversely to the viewing plane of the drawing.

The loop formed by the conveyor belt 8 compasses a chamber 11 connected to a source of negative pressure (not illustrated) and delimited at the bottom by a wall 12 pierced with suction holes 13. As discernible in FIG. 1, the bottom branch 14 of the conveyor belt 8 runs in sliding contact with the wall 12 and is able to retain the particles 15 of tobacco by suction as they emerge from a riser (not illustrated) located underneath the branch 14, thus forming the continuous flow 7 of tobacco.

The flow 7 is directed by the branch 14 of the belt 8 in a substantially horizontal direction 16, transverse to the axis 10 of the pulley 9, onto a feed path 17 running through a preparation zone 18 beneath the feed station 6. The flow 7 of tobacco emerges from the zone 18 in question formed into a continuous ribbon 19 of tobacco filler that will appear substantially constant in section.

The ribbon 19 of tobacco filler proceeds along the feed path 17 in the aforementioned direction 16 toward a station 20 at which the continuous flow 7 is formed into a continuous cigarette rod 21.

To this end, the forming station 20 is occupied by a running strip 22 of paper decoiled from a respective roll 23 by a pair of pinch wheels 24. The decoiling strip 22 is diverted by a pulley 25 and directed toward the forming station 20, which comprises a belt conveyor 26 capable of retaining the strip 22 of paper by suction and advancing it along the feed path 17 together with the ribbon 19 of tobacco filler released onto the selfsame path by the bottom branch 14 of the conveyor belt 8.

The forming station 20 also comprises a beam 27 of conventional embodiment extending along the feed path 17, of which the function is to wrap the paper strip 22 around the ribbon 19 of tobacco filler. The two longitudinal edges of the strip 22 are overlapped gradually along the beam 27 and glued together (in a conventional manner not indicated), thereby generating the aforementioned continuous cigarette rod 21.

The feed path 17 extends beyond the beam 27 and along the feed direction 16 followed by the rod 21 toward a cutting station 28, at which a rotating cutter device 29 divides the continuous rod 21 into cigarette sticks 2 of constant and predetermined length.

Figure 2:
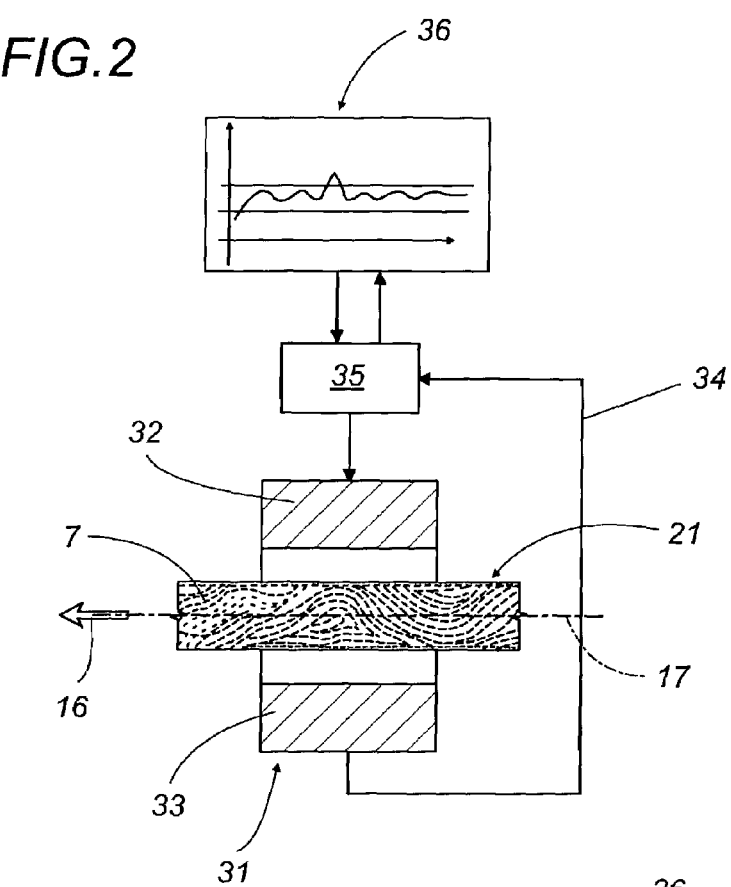
FIGS. 2 and 3 are enlarged details of the device shown in FIG. 1, viewed schematically in side elevation.
Figure 3:
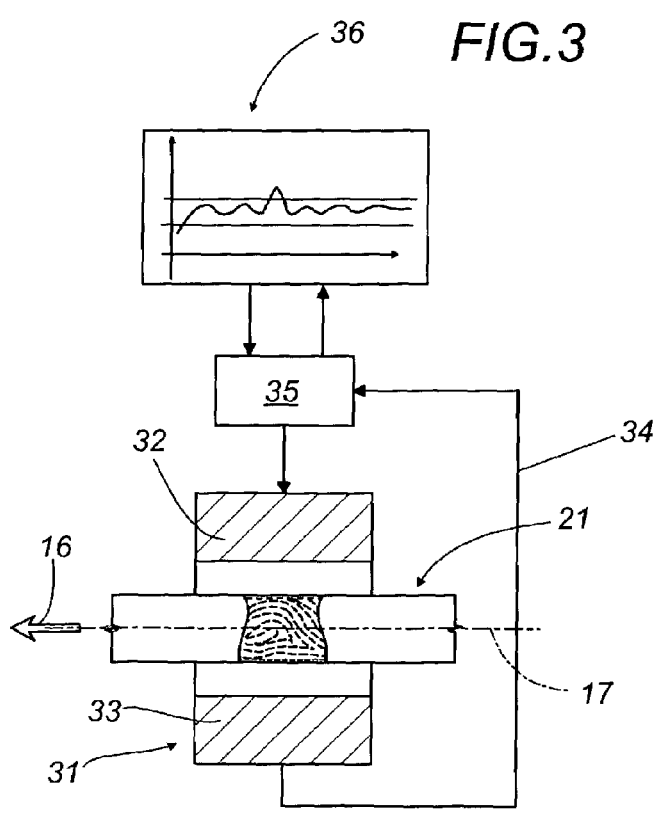

Referring to FIGS. 1, 2 and 3 of the drawings, 30 denotes a device, considered in its entirety, by which foreign bodies in the flow 7 of tobacco are detected and eliminated. The device 30 in question comprises a monitoring device denoted 31 in its entirety, located immediately beyond the beam 27 by which the cigarette rod 21 is formed, comprising (see FIG. 3) an emitter 32 of electromagnetic radiation generated at a predetermined frequency along a direction substantially transverse to and passing through the continuous cigarette rod 21.

The electromagnetic radiation in question falls within the frequency range of microwaves, which are affected neither by the length nor by the color of the fibers in the tobacco particles 15.

The monitoring device 31 further comprises a receiving sensor 33 positioned so as to pick up the electromagnetic radiation after its passage through the flow 7 of tobacco in the cigarette rod 21 and able to generate an output signal 34 indicative of variations in moisture content along the flow 7.

The signal 34 is applied to one input of a master controller 35 of which one output and a further input are connected to a comparator 36 operating in conjunction with the controller 35 and serving to compare the aforementioned signal 34 with one high and predetermined value of constant amplitude that constitutes a preset upper threshold, also with a low and predetermined value of constant amplitude constituting a preset lower threshold.

More exactly, the signal 34 is processed by the controller 35 and relayed to the comparator 36 in the form of a curve 37 reflecting the variations in percentage moisture content within the flow 7 of tobacco per unit of time t. This same curve 37 is compared moment by moment with the constant upper threshold, denoted 38a, and with the constant lower threshold, denoted 38b.

The controller 35 is also connected on the input side to the output of a circuit 39 connected to the cutter device 29 and generating a cyclical output signal 40 indicative of the timing with which the continuous rod 21 is cut into cigarette sticks 2.

This signal 40 allows the controller 35 to sample the moisture curve 37 in such a way that it can be divided into a succession of portions C1, C2, C3, C4 . . . Cn corresponding to elementary signals, each indicating a given portion of the flow 7 of tobacco associated with a uniquely identifiable cigarette stick 2. In the event that the amplitude of the curve 37 should exceed the threshold value 38a, as illustrated by way of example in the case of the portion of the curve denoted C3, the controller 35 will generate a reject signal 43 relative to the cigarette stick 2 associated with that particular portion C3. In like manner, the controller 35 will generate a reject signal 43 if the curve 37 should dip below the lower threshold value 38b.

In any event, the signal 43 is relayed by way of a memory, denoted 41, to a reject device 42 that will proceed, for example utilizing pneumatic or mechanical means of conventional embodiment (not illustrated), to eject the cigarette stick 2 for which an amplitude of the curve 37 greater or less respectively than the upper threshold 38a or the lower threshold 38b has been detected by way of the procedure described above.

The detection in question indicates that there are foreign bodies occupying the part of the flow 7 of tobacco corresponding to the cigarette stick 2 identified, which have the effect of raising or lowering the moisture content within the flow from its correct level.

By way of example, the foreign matter that will raise the moisture content of the flow of tobacco would be paper and the like, whereas the foreign matter tending to lower the moisture content of the flow will be wood, plastic and the like.

Observing the phantom lines of FIGS. 1 and 2, it will be seen that a monitoring device 31 might also be located immediately downstream of the feed station 6, replacing or supplementing a device 31 positioned as described above, in such a way that the electromagnetic radiation is applied directly to the ribbon 19 of tobacco filler rather than to the cigarette rod 21.

What is claimed is:

1. A method of detecting and eliminating foreign bodies in a flow of tobacco, comprising the steps of:
   advancing the flow along a predetermined path in a predetermined direction, passing from a feed station to a preparation zone in which the flow is gathered into a continuous ribbon of tobacco filler, thence through a forming station at which the tobacco filler is incorporated into at least one continuous cigarette rod, and through a cutter device by which the continuous cigarette rod is divided into cigarette sticks;
   exposing the flow of tobacco to electromagnetic radiation of selected frequency;
   detecting the presence of foreign bodies in the flow of tobacco by sensing an output signal indicative of variations in moisture content along the flow of tobacco, the foreign bodies having the effect of modifying the moisture content within the flow from its correct level.

2. A method as in claim 1, comprising the step of comparing the output signal with an upper threshold signal and with a lower threshold signal, both of predetermined and constant amplitude, and sampling the output signal in order to obtain a succession of signals of predetermined duration.

3. A method as in claim 2, wherein the sampling step and the operation of the cutter device are timed mutually in such a way that each signal of predetermined duration can be associated with a portion of the flow of tobacco destined to become the contents of one identifiable cigarette stick.

4. A method as in claim 3, comprising the step of rejecting cigarette sticks, performed following the step of comparing the output signal with the signals of predetermined and constant amplitude.

5. A method as in claims 4, wherein the electromagnetic radiation is in the microwave range of frequencies.

6. A method as in claims 5, wherein the step of exposing the flow of tobacco to electromagnetic radiation of predetermined frequency is performed upstream and/or downstream of the forming station, considered in relation to the feed direction.

7. A method as in claim 3, wherein the electromagnetic radiation is in the microwave range of frequencies.

8. A method as in claim 2, wherein the electromagnetic radiation is in the microwave range of frequencies.

9. A method as in claim 2, wherein step of exposing the flow of tobacco to electromagnetic radiation of predetermined frequency is performed upstream and/or downstream of the forming station, considered in relation to feed direction.

10. A method as in claim 1, wherein the electromagnetic radiation is in the microwave range of frequencies.

11. A method as in claim 1, wherein step of exposing the flow of tobacco to electromagnetic radiation of predetermined frequency is performed upstream and/or downstream of the forming station, considered in relation to feed direction.

12. A method of detecting and eliminating foreign bodies in a flow of tobacco, comprising the steps of:
   advancing the flow along a predetermined path in a predetermined direction, passing from a feed station to a preparation zone in which the flow is gathered into a continuous ribbon of tobacco filler, thence through a forming station at which the tobacco filler is incorporated into at least one continuous cigarette rod, and through a cutter device by which the continuous cigarette rod is divided into cigarette sticks;
   exposing the flow of tobacco to electromagnetic radiation of selected frequency;
   sensing an output signal indicative of variations in moisture content along the flow of tobacco, occasioned by the presence of foreign bodies within the selfsame flow;
   comparing the output signal with an upper threshold signal and with a lower threshold signal, both of predetermined and constant amplitude.

13. A method as in claim 12, comprising the step of rejecting cigarette sticks, performed following the step of comparing the output signal with the signals of predetermined and constant amplitude.

14. A method as in claim 13, wherein the electro-magnetic radiation is in the microwave range of frequencies.

15. A method as in claim 14, wherein the step of exposing the flow of tobacco to electromagnetic radiation of predetermined frequency is performed upstream and/or downstream of the forming station, considered in relation to the feed direction.

16. A method of detecting and eliminating foreign bodies in a flow of tobacco, comprising the steps of:
   advancing the flow along a predetermined path in a predetermined direction, passing from a feed station to a preparation zone in which the flow is gathered into a continuous ribbon of tobacco filler, thence through a forming station at which the tobacco filler is incorporated into at least one continuous cigarette rod, and through a cutter device by which the continuous cigarette rod is divided into cigarette sticks;
   exposing the flow of tobacco to electromagnetic radiation of selected frequency;
   sensing an output signal indicative of variations in moisture content along the flow of tobacco, occasioned by the presence of foreign bodies within the selfsame flow;
   comparing the output signal with an upper threshold signal and with a lower threshold signal, both of predetermined and constant amplitude;
   sampling the output signal in order to obtain a succession of signals of predetermined duration.

17. A method as in claim 16, wherein the sampling step and the operation of the cutter device are timed mutually in such a way that each signal of predetermined duration can be associated with a portion of the flow of tobacco destined to become the contents of one identifiable cigarette stick.

18. A method as in claim 17, comprising the step of rejecting cigarette sticks, performed following the step of comparing the output signal with the signals of predetermined and constant amplitude.

19. A method as in claim 18, wherein the electro-magnetic radiation is in the microwave range of frequencies.

20. A method as in claim 19, wherein the step of exposing the flow of tobacco to electromagnetic radiation of predetermined frequency is performed upstream and/or downstream of the forming station, considered in relation to the feed direction.

* * * * *